US011840578B2

United States Patent
Takahama et al.

(10) Patent No.: US 11,840,578 B2
(45) Date of Patent: Dec. 12, 2023

(54) CALIBRATOR, COMPLEX, AND METHOD FOR MEASURING IGA AGGREGATE

(71) Applicant: SYSMEX CORPORATION, Kobe (JP)

(72) Inventors: Youichi Takahama, Kobe (JP); Hideki Matsuzaki, Kobe (JP); Takuya Kyoutou, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 287 days.

(21) Appl. No.: 17/332,243

(22) Filed: May 27, 2021

(65) Prior Publication Data

US 2021/0371545 A1    Dec. 2, 2021

(30) Foreign Application Priority Data

May 28, 2020 (JP) ................................ 2020-093435

(51) Int. Cl.
| | | |
|---|---|---|
| *C07K 16/42* | (2006.01) | |
| *C07K 16/06* | (2006.01) | |
| *C07K 19/00* | (2006.01) | |
| *G01N 33/68* | (2006.01) | |
| *G01N 33/96* | (2006.01) | |

(52) U.S. Cl.
CPC ........ *C07K 16/4283* (2013.01); *C07K 16/065* (2013.01); *C07K 19/00* (2013.01); *G01N 33/6854* (2013.01); *G01N 33/6893* (2013.01); *G01N 33/96* (2013.01); *G01N 2333/42* (2013.01); *G01N 2333/4724* (2013.01); *G01N 2800/347* (2013.01)

(58) Field of Classification Search
None
See application file for complete search history.

(56) References Cited

U.S. PATENT DOCUMENTS

| | | | |
|---|---|---|---|
| 5,139,932 A | 8/1992 | Cederholm et al. | |
| 8,623,608 B2 * | 1/2014 | Narimatsu | ........... C07K 14/473 435/7.1 |
| 2016/0363586 A1 * | 12/2016 | Tsuruno | ........... G01N 33/57484 |

FOREIGN PATENT DOCUMENTS

JP    6066220 B2    1/2017

OTHER PUBLICATIONS

Geissmann et al. "A Subset of Human Dendritic Cells Expresses IgA Fc Receptor (CD89), Which Mediates Internalization and Activation Upon Cross-Linking by IgA Complexes." J Immunol (2001) 166 (1): 346-352. (Year: 2001).*

Xie et al. "Renal deposition and clearance of recombinant poly-IgA complexes in a model of IgA nephropathy." J Pathol. Jun. 2021; 254(2):159-172. (Year: 2021).*

Mingzhe Ning et al: "Insignificant interference of Elevit in pregnant women serum samples with HBsAg immunoassay on Sysmex", Journal of Clinical Laboratory Analysis, 2019, vol. 33, Issue No. 3, Article No. e22725, 4 pages in total.

(Continued)

*Primary Examiner* — Bao-Thuy L Nguyen
*Assistant Examiner* — Alexander Alexandrovic Volkov
(74) *Attorney, Agent, or Firm* — Sughrue Mion, PLLC (57) ABSTRACT

Disclosed is a calibrator comprising IgA having a biotin group and a biotin-binding site, the calibrator being used to obtain a concentration of an IgA aggregate in a sample.

16 Claims, 2 Drawing Sheets

(56) References Cited

OTHER PUBLICATIONS

Yoshiki Narimatsu et al: "IgA Nephropathy Caused by Unusual Polymerization of IgA1 with Aberrant N-Glycosylation in a Patient with Monoclonal Immunoglobulin Deposition Disease", PLOS ONE, Mar. 20, 2014, vol. 9, Issue No. 3, Article No. e91079, 9 pages in total.
The extended European search report dated Nov. 5, 2021 in a counterpart European patent application No. 21176402.2.

* cited by examiner

CALIBRATOR, COMPLEX, AND METHOD FOR MEASURING IGA AGGREGATE

CROSS REFERENCE TO RELATED APPLICATIONS

This application claims priority from prior Japanese Patent Application No. 2020-093435 filed on May 28, 2020, entitled "Calibrator, complex, and method for measuring IgA aggregate", the entire contents of which are incorporated herein by reference.

FIELD OF THE INVENTION

The present invention relates to a calibrator used to obtain a concentration of an IgA aggregate in a sample. The present invention relates to a complex containing IgA having a biotin group and a biotin-binding site. The present invention relates to a method for measuring an IgA aggregate in a sample using a lectin.

BACKGROUND

PCT International Application Publication No. 2013/172347 A1 describes a method for detecting an IgA aggregate in a sample by an enzyme-linked immunosorbent assay (ELISA) using a lectin that specifically reacts with the IgA aggregate. PCT International Application Publication No. 2013/172347 A1 describes that, comparing a detection result of IgA purified from serum of IgA nephropathy patient and healthy subject, the purified IgA derived from the patient responded particularly strongly to the lectin.

A calibrator is used when a test substance is quantitatively measured by an immunoassay method such as ELISA. A calibrator generally refers to a reagent containing a standard substance corresponding to a test substance. In the field of immunoassay, a standard substance is often a test substance itself isolated or synthesized from a biological sample. However, no suitable calibrator for measurement of IgA aggregate is known. Therefore, an object of the present invention is to provide a calibrator used for measuring an IgA aggregate, a complex containing IgA having a biotin group and a biotin-binding site contained in the calibrator, and a method for measuring an IgA aggregate using the calibrator.

SUMMARY OF THE INVENTION

The scope of the present invention is defined solely by the appended claims, and is not affected to any degree by the statements within this summary.

The present invention provides a calibrator for obtaining a concentration of an IgA aggregate in a sample, comprising: IgA comprising a biotin group; and a biotin-binding site.

The present invention provides a complex for obtaining a concentration of an IgA aggregate in a sample, comprising: IgA comprising a biotin group; and a biotin-binding site.

The present invention provides a method for measuring an IgA aggregate in a sample using a lectin, comprising: obtaining a concentration of the IgA aggregate in the sample using the above-mentioned calibrator or complex.

DETAILED DESCRIPTION OF THE PREFERRED EMBODIMENTS

The method of the present embodiment is a method for measuring an IgA aggregate using a lectin. An IgA aggregate is a multimeric IgA produced by aggregation of IgA in blood of IgA nephropathy patient. At present, it is difficult to separate and purify an IgA aggregate from the blood of IgA nephropathy patient. Therefore, the IgA aggregate itself cannot be used as a calibrator. On the other hand, an IgA monomer without sugar chain abnormalities can be easily obtained. However, such IgA monomer does not bind to a lectin. Therefore, as mentioned above, no suitable calibrator for measurement of IgA aggregate has been known.

The method of the present embodiment is characterized in that a concentration of an IgA aggregate in a sample is obtained using a calibrator containing IgA having a biotin group and a biotin-binding site. The "biotin group" refers to a heterocyclic portion containing an imidazolidine ring in a chemical structure of biotin or its analog. Examples of the biotin analogs include desthiobiotin, oxybiotin, and the like. As used herein, the term "biotin-binding site", "biotin-binding moiety" or "biotin-binding molecule" includes avidin and its analogs or a part of them which binds with a biotin group. Examples of the avidin analogs include streptavidin, neutravidin (trademark), tamavidin (registered trademark), and the like. A biotin-binding site generally exists in a form of a tetramer composed of four subunits. Hereinafter, one molecule of a biotin-binding site will be referred to as "one molecule of streptavidin", and one molecule of a biotin-binding site refers to tetrameric biotin-binding site. One molecule of a biotin-binding site can bind to four biotin groups.

IgA having a biotin group (hereinafter, also referred to as "biotinylated IgA") can be obtained by binding an IgA monomer and biotin or its analog by a known method using a crosslinking agent or the like. Commercially available biotin-labeled reagents may be used. The number of biotin groups contained in one molecule of biotinylated IgA is not particularly limited, and may be one or plural. The IgA monomer may be either natural IgA or recombinant IgA as long as it is of human origin. IgA isotype may be either IgA1 or IgA2. Preferred isotype is IgA1.

Figure 1:
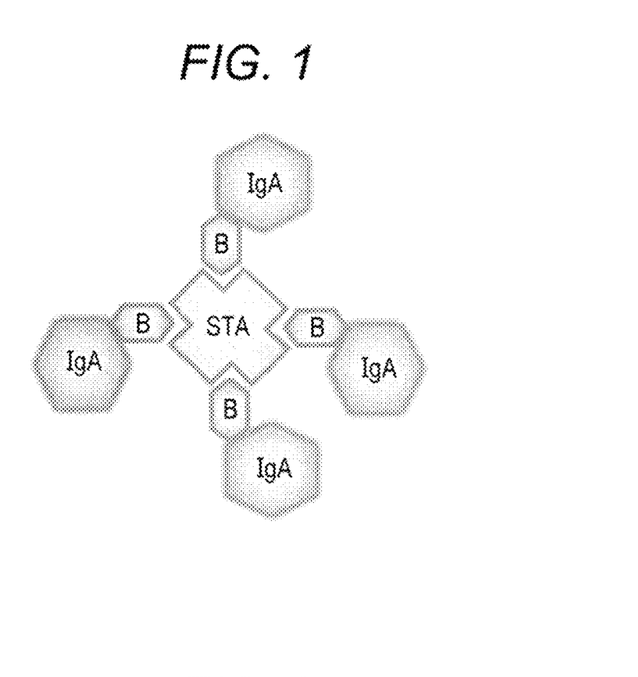
FIG. 1 is a schematic diagram of a complex of IgA having a biotin group and a biotin-binding site.

In the calibrator used in the method of the present embodiment, a complex of biotinylated IgA and a biotin-binding site is formed via a bond between the biotin group and the biotin-binding site. That is, the calibrator is a reagent containing a complex of biotinylated IgA and a biotin-binding site. In the present embodiment, this complex corresponds to a standard substance for IgA aggregate. An example of the complex is shown in FIG. 1 In the figure, "STA" indicates streptavidin and "B" indicates a biotin group. In FIG. 1, four molecules of biotinylated IgA are bound to one molecule of streptavidin, but the present disclosure is not limited to this example. As shown in FIG. 1, the complex of biotinylated IgA and a biotin-binding site is a pseudo-aggregate of IgA. Since this complex can bind to the lectin used for measuring an IgA aggregate, the concentration of the IgA aggregate in the sample can be obtained by using a calibrator containing this complex. In FIG. 1, for convenience, only one biotin group of the biotinylated IgA is shown, but as described above, the biotinylated IgA may have multiple biotin groups.

The complex of biotinylated IgA and a biotin-binding site can be obtained by mixing biotinylated IgA and a biotin-binding site. Mixing conditions are not particularly limited as long as protein is not denatured. For example, a solution of biotinylated IgA and a biotin-binding site may be mixed and stirred or allowed to stand at 4° C. to 40° C. and preferably 15° C. to 37° C.

In the present embodiment, the complex is preferably composed of one molecule of biotin-binding site and two, three or four molecules of biotinylated IgA. When the biotinylated IgA has multiple biotin groups, the complex can theoretically be a macromolecule in which multiple molecules of biotin-binding sites and multiple molecules of biotinylated IgA are bound in a chain. However, such a macromolecule does not actually occur, or even if it does occur, its amount does not affect the method of the present embodiment. Most complexes are complexes of one molecule of biotin-binding site and two, three or four molecules of biotinylated IgA, especially complexes of one molecule of biotin-binding site and four molecules of biotinylated IgA. It is considered that this is because the chain bond between biotinylated IgA and a biotin-binding site does not occur due to causes such as steric hindrance.

In a further embodiment, the calibrator may further contain a polypeptide having a sugar chain that binds to a lectin and a biotin group (hereinafter, also referred to as "biotinylated carrier protein"). The term "polypeptide" refers to a substance in which a plurality of amino acids are bound by peptide bonds, and also includes proteins and fragments thereof, and the like. In this calibrator, a complex of biotinylated IgA, a biotin-binding site and a biotinylated carrier protein is formed via the bond between the biotin group and the biotin-binding site. That is, this calibrator is a reagent containing a complex of biotinylated IgA, a biotin-binding site and a biotinylated carrier protein.

The biotinylated carrier protein can be obtained by binding a polypeptide having a sugar chain that binds to a lectin (hereinafter, also referred to as "carrier protein") and biotin or its analog by a known method using a crosslinking agent or the like. Commercially available biotin-labeled reagents may be used. The number of biotin groups contained in one molecule of biotinylated carrier protein is not particularly limited, and may be one or plural.

The carrier protein is not particularly limited as long as it has a sugar chain to which the lectin used in the method of the present embodiment can be bound. If it is a known lectin, the sequence or structure of the sugar chain to which the lectin specifically binds is known. Examples of the carrier protein include M2BP (Mac-2 binding protein), MUC1 (Mucin 1, cell surface associated glycoprotein), a2M (Alpha-2-macroglobulin) and the like. These carrier proteins are particularly suitable for the method of the present embodiment using WFA (*Wisteria floribunda* agglutinin) as a lectin.

Figure 2:
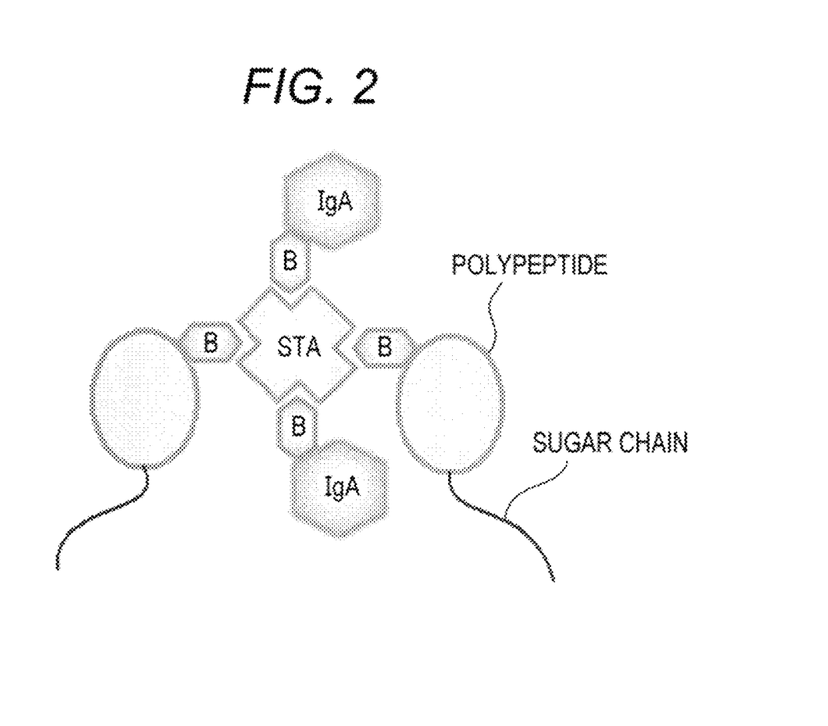
FIG. 2 is a schematic diagram of a complex of IgA having a biotin group, a biotin-binding site, a polypeptide having a sugar chain that binds to a lectin and a biotin group.

In the present embodiment, the complex of biotinylated IgA, a biotin-binding site and a biotinylated carrier protein corresponds to a standard substance for IgA aggregate. An example of this complex is shown in FIG. 2. In FIG. 2, two molecules of biotinylated IgA and two molecules of biotinylated carrier protein are bound to one molecule of streptavidin, but the present disclosure is not limited to this example. As shown in FIG. 2, the complex of biotinylated IgA, a biotin-binding site and a biotinylated carrier protein is a pseudo-aggregate of IgA having a sugar chain to which a lectin is bound. Since this complex can bind to the lectin used for measuring an IgA aggregate by the sugar chain of the biotinylated carrier protein, the concentration of the IgA aggregate in the sample can be obtained by using a calibrator containing this complex. In FIG. 2, for convenience, only one biotin group of the biotinylated IgA and only one biotin group of the biotinylated carrier protein are shown. However, as described above, the biotinylated IgA may have a multiple biotin groups, and the biotinylated carrier protein may have multiple biotin groups.

In the present embodiment, the complex is preferably composed of one molecule of biotin-binding site, one, two or three molecules of biotinylated IgA and one, two or three molecules of biotinylated carrier protein (provided that total number of molecules of biotinylated IgA and biotinylated carrier protein is 2 or more and 4 or less). When the biotinylated IgA and/or the biotinylated carrier protein has multiple biotin groups, the complex can theoretically be a macromolecule in which multiple molecules of biotin-binding sites, multiple molecules of biotinylated IgA and multiple molecules of biotinylated carrier protein are bound in a chain. However, such a macromolecule does not actually occur, or even if it does occur, its amount does not affect the method of the present embodiment.

The complex of biotinylated IgA, a biotin-binding site and a biotinylated carrier protein can be obtained by mixing biotinylated IgA, a biotin-binding site and a biotinylated carrier protein. Mixing conditions are not particularly limited as long as protein is not denatured. For example, a solution of biotinylated IgA, a solution of biotin-binding site and a solution of biotinylated carrier protein may be mixed and stirred or allowed to stand at 4° C. to 40° C. and preferably 15° C. to 37° C. As to the order of mixing, it is preferred that the solution of biotinylated IgA, the solution of biotin-binding site and the solution of biotinylated carrier protein are mixed substantially simultaneously. Alternatively, the solution of biotinylated IgA and the solution of biotinylated carrier protein may be mixed first, and then the obtained solution and the solution of biotin-binding site may be mixed.

The complex contained in the calibrator may be in a form of solid (for example, powder, crystal, freeze-dried product, or the like) or in a form of liquid (for example, solution, suspension, emulsion, or the like). The solvent is not particularly limited as long as it is suitable for storing proteins (particularly antibodies), and examples thereof include physiological saline, buffer solutions, and the like. The buffer solution is a buffer solution having a buffering effect at a pH near neutrality (for example, a pH of 6 or more and 8 or less). Examples of the buffer solution include Good buffers such as HEPES, MES, and PIPES, tris buffered saline (TBS), phosphate buffered saline (PBS), and the like.

The calibrator may contain known additives. Examples of the additive include protein stabilizers such as bovine serum albumin (BSA), preservatives such as sodium azide, inorganic salts such as sodium chloride, and the like.

The calibrator may be in a form of one reagent or in a form of a reagent set including a plurality of reagents. The calibrator, which is one reagent, includes, for example, one container containing a complex of biotinylated IgA and a biotin-binding site, or one container containing a complex of biotinylated IgA, a biotin-binding site and a biotinylated carrier protein.

When the calibrator is a reagent set, each reagent included in the reagent set is hereinafter also referred to as a "calibrator reagent". The calibrator, which is a reagent set, includes a plurality of calibrator reagents each containing a complex of biotinylated IgA and a biotin-binding site, or a plurality of calibrator reagents each containing a complex of biotinylated IgA, a biotin-binding site and a biotinylated carrier protein. In this reagent set, concentrations of the complex in the plurality of calibrator reagents are different from each other. The reagent set includes, for example, a plurality of containers containing each of the plurality of calibrator reagents. The plurality of containers contain complexes at different concentrations.

The number of calibrator reagents included in the reagent set is not particularly limited, but can be selected from, for example, 2, 3, 4, 5 and 6. The concentration of the complex in each calibrator reagent is not particularly limited as long as a calibration curve can be prepared. For example, among the plurality of calibrator reagents, a calibrator reagent having lowest concentration of the complex may contain the complex at a concentration of 1 µg/mL or more and 200 µg/mL or less, and a calibrator reagent having highest concentration of the complex may contain the complex at a concentration of 2 times or more and 1000 times or less the lowest concentration.

In the method of the present embodiment, a concentration of an IgA aggregate in a sample is obtained by measuring the IgA aggregate in the sample using a lectin and also measuring the complex contained in the calibrator. The method for measuring the IgA aggregate in the sample using a lectin will be described below.

In the present embodiment, the sample is not particularly limited as long as it contains or is suspected of containing an IgA aggregate. A preferred sample is a biological sample. Examples of the biological sample include extracellular fluids such as blood (whole blood), plasma, serum, urine, lymph, tissue fluid, cerebrospinal fluid and saliva, and the like. Of these, blood, plasma, serum and urine are preferred. When insoluble contaminants such as cells are contained in the sample, impurities may be removed from the sample by a known means such as centrifugal separation and filtration. The sample may be diluted with an appropriate aqueous medium as necessary. The aqueous medium is not particularly limited as long as it does not interfere with the measurement described later. Examples of the aqueous medium include water, physiological saline, a buffer solution, and the like. The buffer solution is as described above.

Lectin, also called agglutinin, is a protein that specifically binds to a predetermined sugar chain. In the present embodiment, the lectin is not particularly limited as long as it binds to an IgA aggregate. Such lectins themselves are known, such as WFA, HHL (*Hippeastrum* Hybrid lectin), GNA (*Galanthus nivalis* agglutinin), NPA (*Narcissus pseudonarcissus* agglutinin), SBA (Soybean agglutinin), VVA (*Vicia villosa* agglutinin), BPL (*Bauhinia purpurea* lectin), TJA (*Trichosanthes japonica* agglutinin)-II, PHA-L (*Phaseolus vulgaris* leukoagglutinin), AOL (*Aspergillus oryzae* lectin), and the like. Among them, WFA is particularly preferable.

Naturally occurring WFA exists in a tetramer composed of four subunits. A monomeric or dimeric WFA can be obtained from a tetrameric WFA by a known method using a reducing agent or the like. In the present specification, the term "WFA" includes monomeric WFA, dimeric WFA, trimeric WFA and tetrameric WFA, unless the number of subunits is specified. In the present specification, when referring to WFA composed of a predetermined number of subunits, for example, as in "monomeric WFA", "dimeric WFA", "trimeric WFA" and "tetrameric WFA", the number of subunits is clearly written.

In the present embodiment, the WFA may be a tetrameric WFA or may be a monomeric WFA or a dimeric WFA obtained from a tetrameric WFA. Among them, a dimeric WFA is preferable from the point of high reactivity with an IgA aggregate. A method for obtaining a dimer WFA from a tetrameric WFA using a crosslinking agent is described, for example, in U.S. Patent Application Publication No. 2016/0363586 (this document is incorporated herein by reference).

The method for measuring an IgA aggregate using a lectin itself is known, and is described in, for example, Japanese Examined Patent No. 6066220. As such a measurement method, for example, a method based on a principle of ELISA is preferable. Specifically, examples thereof include a method using a lectin that binds to an IgA aggregate, instead of a capture antibody or a detection antibody in the ELISA. The capture antibody is an antibody that specifically binds to a test substance, and is an antibody for capturing the test substance on a solid phase by being immobilized on the solid phase. The detection antibody refers to an antibody that specifically binds to a test substance and has a labeling substance, and provides an antibody that provides a detectable signal via the labeling substance. It is preferable that the detection antibody is not immobilized on a solid phase. For the measurement, an immune complex transfer method described in Japanese Laid-Open Patent Publication No. H1-254868 may be used.

The ELISA may be any of a sandwich method, a competitive method, a direct method, an indirect method, and the like. In a preferred embodiment, the IgA aggregate is measured by sandwich ELISA using a lectin and a capture body containing a labeling substance and specifically binding to the IgA aggregate (hereinafter, also referred to as "labeled capture body"). In this case, the lectin corresponds to the capture antibody in the sandwich ELISA, and the labeled capture body corresponds to the detection antibody in the sandwich ELISA.

The labeled capture body can be obtained by directly or indirectly binding a labeling substance to a capture body that specifically binds to the IgA aggregate. For example, using a crosslinking agent, a commercially available labeling kit or the like, the capture body that specifically binds to the IgA aggregate and the labeling substance may be bound. Alternatively, a labeled secondary antibody against the capture body that specifically binds to the IgA aggregate may be used. The labeled secondary antibody is an antibody that specifically binds to the capture body that specifically binds to the IgA aggregate, and refers to an antibody to which the labeling substance is bound.

The capture body that specifically binds to the IgA aggregate is not particularly limited as long as it is a substance that can bind to a site different from a site to which the lectin binds in the IgA aggregate. Examples of such a capture body include an antibody that specifically binds to IgA (anti-IgA antibody) or an aptamer, an antigen recognized by IgA in the IgA aggregate, and the like.

The labeling substance may be a signal generating substance, or a substance that catalyzes a reaction of other substances to generate a detectable signal. Examples of the signal generating substance include fluorescent substances, radioactive isotopes, and the like. Examples of the substance that catalyzes the reaction of other substances to generate a detectable signal include enzymes. Examples of the enzyme include alkaline phosphatase (ALP), peroxidase, β-galactosidase, glucose oxidase, tyrosinase, acid phosphatase, luciferase, and the like. Examples of the fluorescent substances include fluorescent dyes such as fluorescein isothiocyanate (FITC), rhodamine and Alexa Fluor (registered trademark) and cyanine dyes, fluorescent proteins such as GFP, and the like. Examples of the radioactive isotopes include $^{125}$I, $^{14}$C, $^{32}$P, and the like. Among them, an enzyme is preferable, and ALP is particularly preferable.

An example of a case of measuring a sample and a calibrator by sandwich ELISA will be described below. In this example, an IgA aggregate in the sample is measured and a complex in the calibrator is then measured, but the present disclosure is not limited to this example. The IgA aggregate in the sample may be measured after measuring the complex in the calibrator. Alternatively, the IgA aggregate in the sample and the complex in the calibrator may be measured substantially simultaneously.

First, a measured value of the IgA aggregate is acquired using a sample, a lectin, and a labeled capture body. Specifically, it is as follows. An immune complex containing an IgA aggregate, a lectin and a labeled capture body in the sample is formed on a solid phase. The immune complex can be formed by mixing a sample, a lectin, and a labeled capture body. Moreover, the immune complex can be formed on the solid phase by contacting the immune complex with the solid phase on which the lectin can be immobilized. In the present embodiment, it is preferable to use a solid phase in which the lectin is preliminarily immobilized. That is, the immune complex can be formed on the solid phase by mixing the solid phase on which the lectin is immobilized, the sample, and the labeled capture body.

The mode of immobilization of the lectin on the solid phase is not particularly limited. For example, the lectin and the solid phase may be bound directly, or the lectin and the solid phase may be indirectly bound via another substance. Examples of the direct binding include physical adsorption and the like. Examples of the indirect bond include a bond via a combination of biotin or its analog and a biotin-binding site. In this case, by preliminarily modifying the lectin with biotin or its analog and previously binding a biotin-binding site to the solid phase, the lectin and the solid phase can be indirectly bound via the bond between the biotin or its analog and the biotin-binding site.

The material of the solid phase is not particularly limited. For example, the material can be selected from organic polymer compounds, inorganic compounds, biopolymers, and the like. Examples of the organic polymer compound include latex, polystyrene, polypropylene, and the like. Examples of the inorganic compound include magnetic bodies (iron oxide, chromium oxide, ferrite, and the like), silica, alumina, glass, and the like. Examples of the biopolymer include insoluble agarose, insoluble dextran, gelatin, cellulose, and the like. Two or more of these may be used in combination. The shape of the solid phase is not particularly limited, and examples thereof include particles, microplates, microtubes, membranes, test tubes, and the like. Among them, microplates and particles (particularly magnetic particles) are preferable.

Moreover, the measured value of the IgA aggregate can be acquired by detecting the immune complex formed on the solid phase by a method known in the art. For example, when an anti-IgA antibody to which a labeling substance is bound is used as a labeled capture body, the measured value of the IgA aggregate in the sample can be acquired by detecting a signal generated by the labeling substance. Also when a labeled secondary antibody is used, the measured value of the IgA aggregate in the sample can be acquired in the same manner.

As used herein, the phrase "detecting a signal" includes qualitatively detecting the presence or absence of a signal, quantifying a signal intensity, and semi-quantitatively detecting the intensity of a signal. Semi-quantitative detection means to show the intensity of the signal in stages like "no signal generated", "weak", "medium", "strong", and the like. In the present embodiment, it is preferable to detect the intensity of the signal quantitatively.

The substrate of the enzyme can be appropriately selected from known substrates according to the type of the enzyme. For example, when alkaline phosphatase is used as the enzyme, examples of the substrate include chemiluminescent substrates such as CDP-Star (registered trademark) (disodium 4-chloro-3-(methoxyspiro[1,2-dioxetane-3,2'-(5'-chloro)tricyclo[3.3.1.13,7]decan]-4-yl)phenyl phosphate) and CSPD (registered trademark) (disodium 3-(4-methoxyspiro[1,2-dioxetane-3,2-(5'-chloro)tricyclo[3.3.1.13,7]decan]-4-yl)phenyl phosphate), and chromogenic substrates such as 5-bromo-4-chloro-3-indolyl phosphate (BCIP), disodium 5-bromo-6-chloro-indolyl phosphate and p-nitrophenyl phosphate. When peroxidase is used as the enzyme, examples of the substrate include chemiluminescent substrates such as luminol and derivatives thereof, and chromogenic substrates such as 2,2'-azinobis(3-ethylbenzothiazoline-6-ammonium sulfonate) (ABTS), 1,2-phenylenediamine (OPD) and 3,3',5,5'-tetramethylbenzidine (TMB).

When the labeling substance is a radioactive isotope, radiation as a signal can be measured using a known apparatus such as a scintillation counter. When the labeling substance is a fluorescent substance, fluorescence as a signal can be measured using a known apparatus such as a fluorescence microplate reader. The excitation wavelength and the fluorescence wavelength can be appropriately determined according to the type of fluorescent substance used.

The detection result of the signal can be used as the measured value of the IgA aggregate. For example, when quantitatively detecting a signal intensity, the signal intensity value itself or a value acquired from the measured value can be used as the measured value of the IgA aggregate. Examples of the value acquired from the measured value of the signal intensity include a value obtained by subtracting the measured value of a negative control sample or the background value from the measured value, and the like. The negative control sample can be appropriately selected, and examples thereof include a sample obtained from a healthy subject and the like.

Subsequently, using a calibrator, a lectin and a labeled capture body, a measured value of a complex in the calibrator is acquired. The "complex in the calibrator" refers to a complex of biotinylated IgA and a biotin-binding site, or a complex of biotinylated IgA, a biotin-binding site and a biotinylated carrier protein. Specifically, it is as follows. An immune complex containing the complex in the calibrator, the lectin and the labeled capture body is formed on the solid phase. The immune complex can be formed by mixing a calibrator, a lectin, and a labeled capture body. Moreover, the immune complex can be formed on the solid phase by contacting the immune complex with the solid phase on which the lectin can be immobilized. In the present embodiment, it is preferable to use a solid phase in which the lectin is preliminarily immobilized. That is, the immune complex can be formed on the solid phase by mixing the solid phase on which the lectin is immobilized, the calibrator, and the labeled capture body. Details of the solid phase are as described above.

Moreover, the measured value of the complex in the calibrator can be acquired by detecting the immune complex formed on the solid phase by a method known in the art. For example, when an anti-IgA antibody to which a labeling substance is bound is used as a labeled capture body, the measured value of the complex in the calibrator can be acquired by detecting a signal generated by the labeling substance. Also when a labeled secondary antibody is used, the measured value of the complex in the calibrator can be acquired in the same manner. Details of the signal detection are as described above.

In the present embodiment, it is preferable to measure a plurality of calibrators having different concentrations of the complex. By obtaining the measured values from a plurality of calibrators, a calibration curve described later can be prepared.

In the present embodiment, it is preferable to measure the IgA aggregate in the sample and the calibrator by a sandwich ELISA using a lectin immobilized on a solid phase and an anti-IgA antibody labeled with a labeling substance. When the solid phase is a magnetic particle, measurement may be carried out using a commercially available system such as HISCL series (Sysmex Corporation).

In the present embodiment, B/F(Bound/Free) separation for removing an unreacted free component not forming an immune complex may be performed between formation and detection of the immune complex. The unreacted free component refers to a component not constituting an immune complex. Examples thereof include a lectin and a labeled capture body that did not bind to the IgA aggregate, and the like. The means of B/F separation is not particularly limited, and when the solid phase is a particle, B/F separation can be performed by recovering only the solid phase capturing the immune complex by centrifugation. When the solid phase is a container such as a microplate or a microtube, B/F separation can be performed by removing a liquid containing an unreacted free component. When the solid phase is a magnetic particle, B/F separation can be performed by aspirating and removing a liquid containing an unreacted free component by a nozzle while magnetically constraining the magnetic particles with a magnet, which is preferable from the viewpoint of automation. After removing the unreacted free component, the solid phase capturing the immune complex may be washed with a suitable aqueous medium such as PBS.

In the present embodiment, the concentration of the IgA aggregate in the sample is obtained from the measured value of the IgA aggregate in the sample and the measured value of the complex in the calibrator. The concentration of the IgA aggregate in the sample includes not only commonly used concepts of concentration (for example, mass ratio, volume ratio, mole fraction, mass per unit volume, number of moles per unit volume, etc.), but also values that serve as indexes of the concentration. Examples of the values that serve as indexes of the concentration include a number (grade) that semi-quantitatively indicates the concentration of the IgA aggregate in the sample, and the like.

Since the concentration of the complex in the calibrator is known, the concentration of the IgA aggregate in the sample can be calculated from the measured value of the IgA aggregate based on the measured value of the complex. In a preferred embodiment, a calibration curve is prepared from the measured values of the complex, and the concentration of the IgA aggregate in the sample is obtained based on the calibration curve and the measured value of the IgA aggregate. The calibration curve can be prepared, for example, by plotting the measured values of the complex acquired from a plurality of calibrators on an XY plane in which the concentration of the complex in the calibrator is taken on an X-axis and the measured values (for example, signal intensities) are taken on a Y-axis to obtain a straight line or a curve by a known method such as a least squares method. By applying the measured value of the IgA aggregate to the calibration curve, the concentration of the IgA aggregate in the sample can be obtained.

Currently, IgA nephropathy is diagnosed only by renal biopsy. On the other hand, as described above, it is known that the IgA aggregate is increased in blood and urine of IgA nephropathy patient. Therefore, the concentration of the IgA aggregate obtained by the method of the present embodiment may be used to determine whether or not a subject has IgA nephropathy. For example, the present disclosure provides a method of assisting determination of IgA nephropathy. This method includes measuring an IgA aggregate in a sample obtained from a subject using a lectin and obtaining the concentration of the IgA aggregate in the sample using a calibrator containing IgA having a biotin group and a biotin-binding site. In this method, a fact that the concentration of the IgA aggregate is equal to or higher than a predetermined threshold suggests that the subject has a high risk of having IgA nephropathy.

In a further embodiment, a method of assisting determination of IgA nephropathy includes acquiring a measured value of an IgA aggregate in a sample, using the sample obtained from a subject, and a lectin and a capture body containing a labeling substance and specifically binding to the IgA aggregate, acquiring a measured value of the complex in the calibrator using the calibrator, the lectin, and the capture body, and obtaining the concentration of the IgA aggregate in the sample from the measured value of the IgA aggregate and the measured value of the complex. The method of assisting determination of IgA nephropathy may be a method in which a fact that the concentration of the IgA aggregate is equal to or higher than a predetermined threshold suggests that the subject has a high risk of having IgA nephropathy.

The predetermined threshold is not particularly limited. The predetermined threshold can be appropriately set. For example, biological samples are collected from each of a healthy subject group and an IgA nephropathy patient group, and concentrations of IgA aggregates in the samples are obtained by the method of the present embodiment. For the obtained concentration data of IgA aggregates, a value that can most accurately distinguish between the healthy subject group and the patient group is determined, and the value is set as a threshold value. In setting the threshold value, sensitivity, specificity, positive predictive value, negative predictive value, and the like may be considered.

A further embodiment is a calibrator containing biotinylated IgA and a biotin-binding site, which is used to obtain a concentration of an IgA aggregate in a sample. The calibrator of the present embodiment may further include a biotinylated carrier protein. The calibrator of the present embodiment is suitably used for the method of the present embodiment described above. Details of the calibrator are the same as those described for the method of the present embodiment.

In one embodiment, the calibrator is a reagent containing a complex of biotinylated IgA and a biotin-binding site. In a further embodiment, the calibrator is a reagent containing a complex of biotinylated IgA, a biotin-binding site and a biotinylated carrier protein. Details of these complexes are the same as those described for the method of the present embodiment. The reagent may be in a form of a container containing the complex. The container may be packed in a box and provided to a user. The box may contain an attached document. Composition, usage, storage method, etc. of the calibrator of the present embodiment may be described in the attached document.

Figure 3:
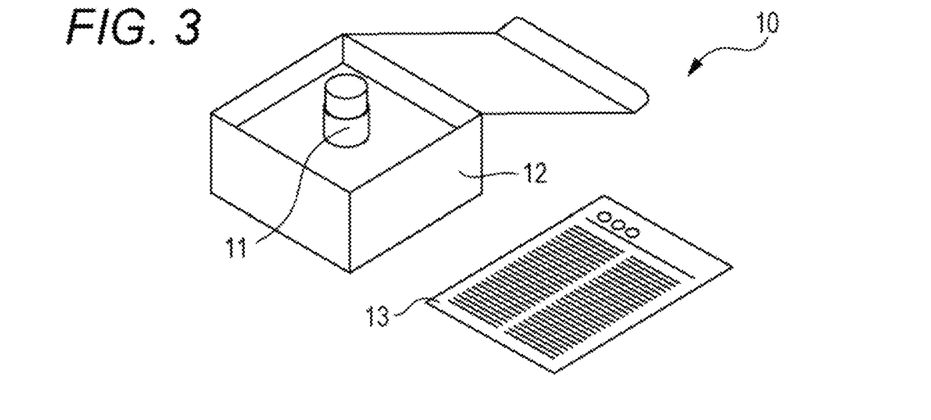
FIG. 3 is a schematic diagram of a calibrator in a form of one reagent.

An example of the calibrator is shown in FIG. 3. In FIG. 3, 10 denotes a calibrator of the present embodiment, 11 denotes a first container containing a complex of biotinylated IgA and a biotin-binding site, or a complex of biotinylated IgA, a biotin-binding site and a biotinylated carrier protein, 12 denotes a packing box, and 13 denotes an attached document. FIG. 3 shows a calibrator in a form of one reagent, but the present disclosure is not limited thereto. The calibrator may be in a form of a reagent set including a plurality of calibrator reagents. Details of the calibrator, which is a reagent set, are the same as those described for the method of the present embodiment.

Figure 4:
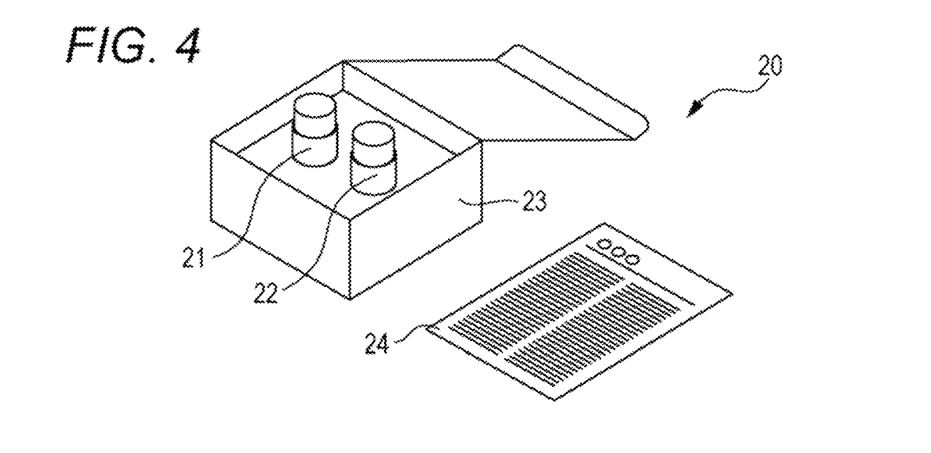
FIG. 4 is a schematic diagram of a calibrator in a form of a reagent set including a plurality of reagents.

In a further embodiment, the calibrator is a reagent set including a reagent containing biotinylated IgA and a reagent containing a biotin-binding site. The complex of biotinylated IgA and a biotin-binding site can be obtained by mixing the reagent containing biotinylated IgA and the reagent containing a biotin-binding site. Details of the mixing conditions are the same as those described for the method of the present embodiment. An example of this calibrator is shown in FIG. 4. In FIG. 4, 20 denotes a calibrator of the present embodiment, 21 denotes a first container containing biotinylated IgA, 22 denotes a second container containing a biotin-binding site, 23 denotes a packing box, and 24 denotes an attached document.

Figure 5:
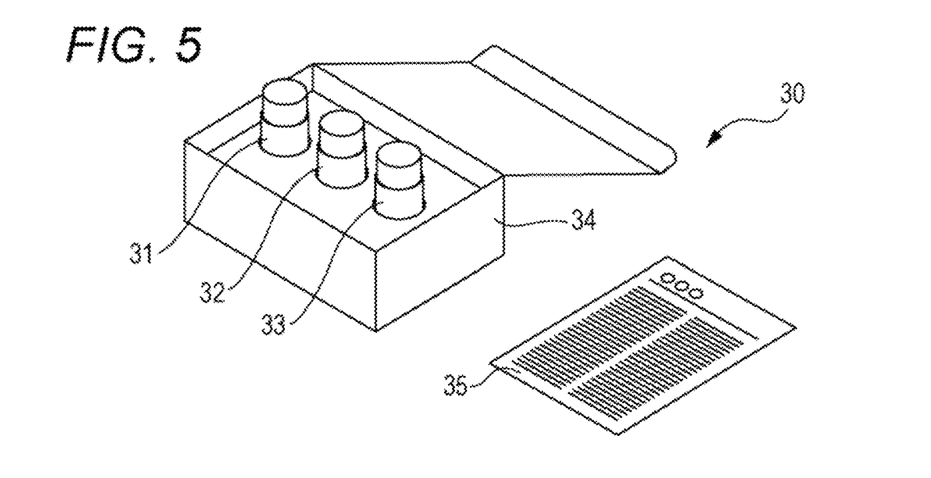
FIG. 5 is a schematic diagram of a calibrator in a form of a reagent set including a plurality of reagents.

In a further embodiment, the calibrator is a reagent set including a reagent containing biotinylated IgA, a reagent containing a biotin-binding site, and a reagent containing a biotinylated carrier protein. The complex of biotinylated IgA, a biotin-binding site, and a biotinylated carrier protein can be obtained by mixing a reagent containing biotinylated IgA, a reagent containing a biotin-binding site, and a reagent containing a biotinylated carrier protein. Details of the mixing conditions are the same as those described for the method of the present embodiment. An example of this calibrator is shown in FIG. 5. In FIG. 5, 30 denotes a calibrator of the present embodiment, 31 denotes a first container containing biotinylated IgA, 32 denotes a second container containing a biotin-binding site, 33 denotes a third container containing a biotinylated carrier protein, 34 denotes a packing box, and 35 denotes an attached document.

A further embodiment is a complex containing biotinylated IgA and a biotin-binding site, which is used to obtain a concentration of an IgA aggregate in a sample. The complex of the present embodiment may be a complex of biotinylated IgA and a biotin-binding site, or a complex of biotinylated IgA, a biotin-binding site and a biotinylated carrier protein. The complex of the present embodiment is suitably used for the method of the present embodiment described above. Details of the complex of the present embodiment are the same as those described for the method of the present embodiment.

A further embodiment is a use of IgA and a biotin-binding site having a biotin group, for production of a calibrator used to obtain a concentration of an IgA aggregate in a sample. In the present embodiment, a calibrator containing a complex of IgA having a biotin group and a biotin-binding site can be obtained by mixing IgA having a biotin group and a biotin-binding site.

A further embodiment is a use of IgA having a biotin group, a biotin-binding site, and a polypeptide having a sugar chain that binds to a lectin and a biotin group, for production of a calibrator used to obtain a concentration of an IgA aggregate in a sample. In the present embodiment, the calibrator containing a complex of biotinylated IgA, a biotin-binding site and a biotinylated carrier protein can be obtained by mixing biotinylated IgA, a biotin-binding site and a biotinylated carrier protein.

Hereinafter, the present disclosure will be described in more detail by examples, but the present disclosure is not limited to these examples.

EXAMPLES

Example 1

1. Preparation of Measurement Reagents
(1.1) Buffer Solution for Sample Dilution (First Reagent)
10 mM HEPES (pH 7.5) containing 1% BSA was prepared as a buffer solution for sample dilution.
(1.2) Magnetic Particle on which WFA is Immobilized (Second Reagent)
A WFA-containing solution (WFA concentration 2.5 mg/mL) was obtained by adding WFA lectin (Vector Laboratories) to 20 mM PBS (pH 7.5). 5-(N-Succinimidyloxycarbonyl) pentyl D-biotinamide (Biotin-AC5-Osu, DOJINDO LABORATORIES) which is a crosslinking agent having a biotin group was added to this WFA-containing solution so that the WFA/crosslinking agent (molar ratio) would be 1/100. The resulting solution was incubated at 25° C. for 90 minutes to react the WFA with the crosslinking agent. The resulting reaction product was purified by HPLC to obtain a biotinylated dimer WFA. For HPLC, PBS (pH 6.5) was used as an elution solvent, and a gel filtration column (TSKGEL® G3000SWXL, Tosoh Corporation) was used as a separation column. A HISCL® R2 reagent (Sysmex Corporation) was used as a suspension containing a streptavidin-coupled magnetic particle. The biotinylated dimeric WFA and the HISCL® R2 reagent were mixed and reacted so that concentration of the biotinylated dimeric WFA would be 20 μg/mL. The resulting reaction product was washed three times with a 100 mM MES buffer solution (pH 6.5) to obtain a magnetic particle on which the dimeric WFA was immobilized (hereinafter also referred to as "WFA-immobilized particle").
(1.3) Solution Containing ALP-Labeled Anti-IgA Antibody (Third Reagent)
As an anti-IgA antibody, an anti-human IgA antibody (SouthernBiotech) was used. This anti-IgA antibody and bovine small intestine-derived ALP (Oriental Yeast Co., Ltd.) were bound to each other using a maleimide crosslinking agent and purified by affinity chromatography to obtain a solution containing an ALP-labeled anti-IgA antibody.
(1.4) Measurement Buffer Solution (Fourth Reagent) and Substrate Solution (Fifth Reagent)
As a measurement buffer solution, a HISCL® R4 reagent (Sysmex Corporation) was used. As a substrate solution, a HISCL® R2 reagent (Sysmex Corporation) containing CDP-STAR™ (Applied Biosystems) as a chemiluminescent substrate of ALP was used.

2. Preparation of Calibrator
(2.1) Preparation of IgA Having Biotin Group

As an IgA monomer, human IgA (Native Human IgA protein, Abcam) was used. Human IgA was added to 20 mM PBS (pH 7.5) to obtain an IgA solution. A crosslinking agent Biotin-AC5-Osu (DOJINDO LABORATORIES) was added to this IgA solution so that the IgA/crosslinking agent (molar ratio) would be $1/100$. The resulting solution was incubated at 25° C. for 90 minutes to obtain biotinylated IgA.

(2.2) Preparation of Polypeptide Having Sugar Chain that Binds to Lectin and Biotin Group As carrier proteins, M2BP (Sysmex product), MUC1 (Sysmex product) and a2M (Sigma-Aldrich) were used. Each carrier protein was added to 20 mM PBS (pH 7.5) to obtain solutions of the carrier protein. A crosslinking agent Biotin-AC5-Osu (DOJINDO LABORATORIES) was added to this solution so that the carrier protein/crosslinking agent (molar ratio) would be $1/100$. The resulting solution was incubated at 25° C. for 90 minutes to obtain biotinylated carrier proteins.

(2.3) Preparation of Complex of Biotinylated IgA and Streptavidin

A solution containing biotinylated IgA and a solution containing streptavidin (Streptavidin SQ, Roche Diagnostics K.K.) were mixed and allowed to stand at room temperature for 1 hour to obtain a complex of biotinylated IgA and streptavidin (hereinafter, also referred to as "IgA-Bio-STA-Bio-IgA").

(2.4) Preparation of Complex of Biotinylated IgA, Streptavidin and Biotinylated Carrier Protein A solution of each biotinylated carrier protein was mixed with a solution containing biotinylated IgA. The resulting mixed solution and a solution containing streptavidin (Streptavidin SQ, Roche Diagnostics Co., Ltd.) were mixed and allowed to stand at room temperature for 1 hour to obtain a complex (0.2 mg/mL) of biotinylated IgA, a biotinylated carrier protein and streptavidin. Hereinafter, a complex containing M2BP is also referred to as "M2BP-Bio-STA-Bio-IgA", a complex containing MUC1 is also referred to as "MUC1-Bio-STA-Bio-IgA", and a complex containing α2M is also referred to as "A2M-Bio-STA-Bio-IgA".

3. Measurement of Calibrator (1)

M2BP-Bio-STA-Bio-IgA, MUC1-Bio-STA-Bio-IgA and A2M-Bio-STA-Bio-IgA were measured respectively as calibrators, with a fully automated immunoassay system HISCL (registered trademark) 5000 (Sysmex Corporation) using the first to fifth reagents. A measurement procedure according to HISCL-5000 was as follows. After mixing the calibrator (30 μL) and the first reagent (100 μL), the second reagent (30 μL) was added thereto. The magnetic particles in the obtained mixed solution were magnetically collected to remove the supernatant, and a HISCL washing solution (300 μL) was added to wash the magnetic particles. The supernatant was removed, and the third reagent (100 μL) was added to the magnetic particle and mixed. The magnetic particles in the obtained mixed solution were magnetically collected to remove the supernatant, and a HISCL washing solution (300 μL) was added to wash the magnetic particles. Supernatant was removed, and the fourth reagent (50 μL) and the fifth reagent (100 μL) were added to the magnetic particle, and the chemiluminescence intensity was measured. As controls, streptavidin (STA) and each biotinylated carrier protein (M2BP-Bio, MUC1-Bio and A2M-Bio) were similarly measured.

Table 1 shows the measured values (signal counts).

TABLE 1

| Calibrator | Count |
| --- | --- |
| STA | 531 |
| M2BP-Bio | 532 |
| MUC1-Bio | 542 |
| A2M-Bio | 1,279 |
| M2BP-Bio-STA-Bio-IgA | 144,375 |
| MUC1-Bio-STA-Bio-IgA | 201,568 |
| A2M-Bio-STA-Bio-IgA | 659,882 |

As shown in Table 1, significantly high signal counts were obtained when measuring M2BP-Bio-STA-Bio-IgA, MUC1-Bio-STA-Bio-IgA and A2M-Bio-STA-Bio-IgA. Therefore, it was shown that M2BP-Bio-STA-Bio-IgA, MUC1-Bio-STA-Bio-IgA and A2M-Bio-STA-Bio-IgA can be used as calibrators for an immunoassay method using a lectin and an anti-IgA antibody.

4. Measurement of Calibrator (2)

As calibrators, M2BP-Bio-STA-Bio-IgA, MUC1-Bio-STA-Bio-IgA, A2M-Bio-STA-Bio-IgA and IgA-Bio-STA-Bio-IgA were used. Measurements were carried out in the same manner as above, except that each calibrator was diluted 5-fold, 25-fold and 125-fold with 20 mM PBS (pH 7.5). Table 2 shows the measured values (signal counts).

TABLE 2

| | Dilution ratio | | |
| --- | --- | --- | --- |
| Calibrator | 125 | 25 | 5 |
| M2BP-Bio-STA-Bio-IgA | 2,876 | 17,908 | 123,638 |
| MUC1-Bio-STA-Bio-IgA | 1,800 | 10,554 | 42,952 |
| A2M-Bio-STA-Bio-IgA | 6,269 | 39,398 | 230,135 |
| IgA-Bio-STA-Bio-IgA | 1,078 | 4,263 | 38,048 |

As shown in Table 2, the measured values fluctuated according to the dilution ratio regardless of which calibrator was used. Therefore, it was shown that M2BP-Bio-STA-Bio-IgA, MUC1-Bio-STA-Bio-IgA and A2M-Bio-STA-Bio-IgA can be used as calibrators for quantifying a concentration of an IgA aggregate in the immunoassay method using a lectin and an anti-IgA antibody.

What is claimed is:

1. A calibrator for obtaining a concentration of an IgA aggregate in a sample, comprising:
   IgA comprising a biotin group;
   a biotin-binding site; and
   a polypeptide comprising: a sugar chain that binds to a lectin; and a biotin group.

2. The calibrator according to claim 1, which is a reagent composition comprising a complex of: the IgA comprising a biotin group; the biotin-binding site; and the polypeptide.

3. The calibrator according to claim 1, which is a reagent set comprising:
   a reagent composition comprising the IgA comprising a biotin group;
   a reagent composition comprising the biotin-binding site; and
   a reagent composition comprising the polypeptide.

4. The calibrator according to claim 1, wherein the calibrator is a reagent set comprising a plurality of reagent compositions each comprising a complex of: the IgA comprising a biotin group; the biotin-binding site; and the polypeptide, and concentrations of the complex in the plurality of reagents are different from each other.

5. The calibrator according to claim 1, wherein the polypeptide comprises all or part of at least one glycoprotein selected from a group consisting of M2BP, MUC1 and α2M.

6. The calibrator according to claim 1, wherein the IgA is IgA1.

7. A complex for obtaining a concentration of an IgA aggregate in a sample, comprising:
   IgA comprising a biotin group;
   a biotin-binding site; and
   a polypeptide comprising: a sugar chain that binds to a lectin; and a biotin group.

8. A method for measuring an IgA aggregate in a sample using a lectin, comprising:
   obtaining a concentration of the IgA aggregate in the sample using a calibrator comprising: IgA comprising a biotin group; and a biotin-binding site.

9. The method according to claim 8, comprising:
   acquiring a measured value of the IgA aggregate using the sample, the lectin, and a capture body that comprises a labeling substance and specifically binds to the IgA aggregate;
   acquiring a measured value of the complex comprising: the IgA comprising a biotin group; and the biotin-binding site, using the calibrator, the lectin, and the capture body; and
   obtaining a concentration of the IgA aggregate in the sample from the measured value of the IgA aggregate and the measured value of the complex.

10. The method according to claim 9, wherein
   in the obtaining of the concentration of the IgA aggregate,
   a calibration curve is prepared from the measured value of the complex, and
   the concentration of the IgA aggregate in the sample is obtained based on the calibration curve and the measured value of the IgA aggregate.

11. The method according to claim 8, wherein the lectin is immobilized on a solid phase.

12. The method according to claim 8, wherein the lectin is at least one lectin selected from a group consisting of WFA, HHL, GNA, NPA, SBA, VVA, BPL, TJA-II, PHA-L and AOL.

13. The method according to claim 8, which is a reagent composition comprising a complex of: the IgA comprising a biotin group; and the biotin-binding site.

14. The method according to claim 8, wherein the calibrator is a reagent set comprising a plurality of reagent compositions each comprising a complex of: the IgA comprising a biotin group; and the biotin-binding site, and
   concentrations of the complex in the plurality of reagent compositions are different from each other.

15. The method according to claim 8, further comprising a polypeptide comprising: a sugar chain that binds to a lectin; and a biotin group.

16. The method according to claim 15, wherein the calibrator is a reagent set comprising a plurality of reagent compositions each comprising a complex of: the IgA comprising a biotin group; the biotin-binding site; and the polypeptide, and
   concentrations of the complex in the plurality of reagents are different from each other.

* * * * *